(12) United States Patent
Arai (10) Patent No.: US 11,484,275 B2
(45) Date of Patent: Nov. 1, 2022

(54) IMAGE PROCESSING APPARATUS, METHOD, AND PROGRAM

(71) Applicant: FUJIFILM Corporation, Tokyo (JP)

(72) Inventor: Takahisa Arai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 207 days.

(21) Appl. No.: 16/924,786

(22) Filed: Jul. 9, 2020

(65) Prior Publication Data

US 2021/0030373 A1 Feb. 4, 2021

(30) Foreign Application Priority Data

Jul. 29, 2019 (JP) .............................. JP2019-138864

(51) Int. Cl.
*A61B 6/02* (2006.01)
*A61B 6/00* (2006.01)
*G06T 11/00* (2006.01)

(52) U.S. Cl.
CPC .............. *A61B 6/025* (2013.01); *A61B 6/502* (2013.01); *G06T 11/005* (2013.01); *G06T 11/008* (2013.01)

(58) Field of Classification Search
None
See application file for complete search history.

(56) References Cited

U.S. PATENT DOCUMENTS

| 2009/0123052 | A1* | 5/2009 | Ruth | ...................... | A61B 6/502 |
| | | | | | 382/132 |
| 2013/0251223 | A1* | 9/2013 | Smith | ...................... | G06T 5/003 |
| | | | | | 382/131 |
| 2018/0055459 | A1 | 3/2018 | Fukuda | | |
| 2020/0146645 | A1 | 5/2020 | Nakayama | | |

FOREIGN PATENT DOCUMENTS

| JP | 2014-128716 A | 7/2014 |
| JP | 2018-029746 A | 3/2018 |
| WO | 2019/017442 A1 | 1/2019 |

OTHER PUBLICATIONS

An Office Action; "Notice of Reasons for Refusal", mailed by the Japanese Patent Office dated Jun. 7, 2022, which corresponds to Japanese Patent Application No. 2019-138864 and is related to U.S. Appl. No. 16/924,786; with English language translation.

* cited by examiner

*Primary Examiner* — Vu Le
*Assistant Examiner* — Courtney Joan Nelson
(74) *Attorney, Agent, or Firm* — Studebaker & Brackett PC (57) ABSTRACT

A common area derivation unit derives a common area common to at least a part of a plurality of projection images corresponding to a plurality of radiation source positions which are generated by causing an imaging apparatus to perform tomosynthesis imaging in which a radiation source is moved relative to a detection unit to irradiate a subject with radiation at the plurality of radiation source positions according to movement of the radiation source. A display control unit emphasizes effective image areas, corresponding to the common area, of at least a part of a plurality of tomographic images representing a plurality of tomographic planes of the subject which are generated by reconstructing the plurality of projection images, or a composite two-dimensional image generated from the plurality of tomographic images, and displays at least the part of the tomographic images or the composite two-dimensional image on a display.

7 Claims, 12 Drawing Sheets

| COMPRESSION THICKNESS (mm) | COMMON AREA WIDTH L0 (mm) |
|---|---|
| 10 | 232 |
| 20 | 228 |
| 149 | 181 |

TBL1

IMAGE PROCESSING APPARATUS, METHOD, AND PROGRAM

CROSS REFERENCE TO RELATED APPLICATIONS

The present application claims priority under 35 U.S.C. § 119 to Japanese Patent Application No.2019-138864 filed on Jul. 29, 2019. The above application is hereby expressly incorporated by reference, in its entirety, into the present application.

BACKGROUND

Technical Field

The present disclosure relates to an image processing apparatus, a method, and a program.

Related Art

In recent years, in order to promote early detection of breast cancer, image diagnosis using a radiation image capturing apparatus (called mammography) for imaging a breast has attracted attention. Further, tomosynthesis imaging has been proposed in which in the mammography, imaging is performed by moving a radiation source to irradiate a breast with radiation at a plurality of radiation source positions and a plurality of projection images acquired by the imaging are added up to generate a tomographic image in which a desired tomographic plane is emphasized. In the tomosynthesis imaging, a plurality of projection images are acquired by imaging the breast at a plurality of radiation source positions by moving the radiation source in parallel to a radiation detector or moving the radiation source so as to draw a circular or elliptical arc according to the characteristics of the imaging apparatus and required tomographic images, and the projection images are reconstructed using, for example, a back projection method, such as a simple back projection method or a filtered back projection method, to generate a tomographic image.

By generating such a tomographic image on a plurality of tomographic planes of the breast, it is possible to separate structures overlapping each other in a depth direction in which the tomographic planes are aligned, in the breast. For this reason, by performing diagnosis using a tomographic image generated by performing tomosynthesis imaging, it is possible to find the lesion difficult to be detected in a two-dimensional image acquired by simple imaging in the related art (hereinafter, referred to as a simple two-dimensional image).

A technique has been known in which a pseudo two-dimensional image (hereinafter, referred to as a composite two-dimensional image) corresponding to the simple two-dimensional image is generated by using a plurality of the tomographic images that are acquired by tomosynthesis imaging and have different distances (a position in a height direction) toward the radiation source side from the detection surface of the radiation detector (JP2014-128716A).

Meanwhile, in mammography, the breast is imaged while being placed on an imaging table and pressed by a compression plate. For this reason, an edge of the compression plate appears as a linear artifact in the image acquired by imaging. In a case where the edge of the compression plate is bent upward to form side walls, the side walls appear as a band-shaped image (hereinafter, referred to as an edge image) in the image. In tomosynthesis imaging, since the radiation source is moved to image the breast, in particular, in a case where the breast is irradiated with radiation from a direction inclined with respect to the vertical line to the detection surface of the radiation detector, the range in which the projection image includes the edge image of the compression plate becomes large. For this reason, in a case where the tomographic image is generated, the tomographic image is reconstructed using only the area excluding the edge image from the projection image, so that artifacts caused by the edge image are not included in the tomographic image and the composite two-dimensional image.

In tomosynthesis imaging, as described above, the radiation source is moved to image the breast. For this reason, in each of the plurality of projection images acquired by the tomosynthesis imaging, the ranges in which the breast image is included are different. At the time of reconstruction, the image quality of the generated tomographic image becomes high as the number of used projection images increases. For this reason, in the tomographic image and the composite two-dimensional image, the area common to all of the plurality of projection images has a high image quality, but as the number of projection images used for reconstruction decreases, the quality of the tomographic image and the composite two-dimensional image become low. For this reason, in the tomographic image and the composite two-dimensional image, a high-quality area and a low-quality area are distributed in a band shape in the movement direction of the radiation source.

In mammography, it is important from the viewpoint of diagnosis to find lesions such as tumors and calcifications hidden in mammary gland tissue and metastasis to lymph nodes. However, in a portion where the image quality of the tomographic image and the composite two-dimensional image deteriorates, it is difficult to find a lesion during image reading. In a case where it is difficult to find a lesion, the possibility of erroneous diagnosis due to missing the lesion increases.

SUMMARY OF THE INVENTION

The present disclosure has been made in view of the above circumstances, and an object of the present disclosure is to reduce the possibility of erroneous diagnosis during image reading using the tomographic image acquired by tomosynthesis imaging and the composite two-dimensional image.

An image processing apparatus according to the present disclosure comprises a common area derivation unit that derives a common area common to at least a part of a plurality of projection images corresponding to a plurality of radiation source positions which are generated by causing an imaging apparatus to perform tomosynthesis imaging in which a radiation source is moved relative to a detection unit to irradiate a subject with radiation at the plurality of radiation source positions according to movement of the radiation source, and a display control unit that emphasizes effective image areas, corresponding to the common area, of at least a part of a plurality of tomographic images representing a plurality of tomographic planes of the subject which are generated by reconstructing the plurality of projection images, or a composite two-dimensional image generated from the plurality of tomographic images, and displays at least the part of the tomographic images or the composite two-dimensional image on a display unit.

In the image processing apparatus according to the present disclosure, in a case where a width of the common area in a movement direction of the radiation source is equal to or greater than a predetermined threshold value, the display control unit may display at least the part of the plurality of tomographic images or the composite two-dimensional image on the display unit.

In the image processing apparatus according to the present disclosure, in a case where the width of the common area in the movement direction of the radiation source is smaller than the predetermined threshold value, the display control unit may display a warning screen on the display unit.

The image processing apparatus according to the present disclosure may further comprise a reconstruction unit that reconstructs the plurality of projection images to generate the plurality of tomographic images.

The image processing apparatus according to the present disclosure may further comprise a synthesis unit that generates the composite two-dimensional image from the plurality of tomographic images.

In this case, the synthesis unit may generate the composite two-dimensional image by weighted-adding pixel values of pixels corresponding to the plurality of tomographic images.

An image processing method according to the present disclosure comprises deriving a common area common to at least a part of a plurality of projection images corresponding to a plurality of radiation source positions which are generated by causing an imaging apparatus to perform tomosynthesis imaging in which a radiation source is moved relative to a detection unit to irradiate a subject with radiation at the plurality of radiation source positions according to movement of the radiation source, and emphasizing effective image areas, corresponding to the common area, of at least a part of a plurality of tomographic images representing a plurality of tomographic planes of the subject which are generated by reconstructing the plurality of projection images, or a composite two-dimensional image generated from the plurality of tomographic images, and displaying at least the part of the tomographic images or the composite two-dimensional image on a display unit.

The image processing method according to the present disclosure may be provided as a program causing a computer to execute the method steps.

Another image processing apparatus according to the present disclosure comprises a memory that stores a command to be executed by a computer, and a processor configured to execute the stored commands, in which the processor executes deriving a common area common to at least a part of a plurality of projection images corresponding to a plurality of radiation source positions which are generated by causing an imaging apparatus to perform tomosynthesis imaging in which a radiation source is moved relative to a detection unit to irradiate a subject with radiation at the plurality of radiation source positions according to movement of the radiation source, and a procedure of emphasizing effective image areas, corresponding to the common area, of at least a part of a plurality of tomographic images representing a plurality of tomographic planes of the subject which are generated by reconstructing the plurality of projection images, or a composite two-dimensional image generated from the plurality of tomographic images, and displaying at least the part of the tomographic images or the composite two-dimensional image on a display unit.

According to the present disclosure, it is possible to reduce the possibility of missing a lesion in a tomographic image acquired by tomosynthesis imaging and a composite two-dimensional image.

DETAILED DESCRIPTION

Figure 1:
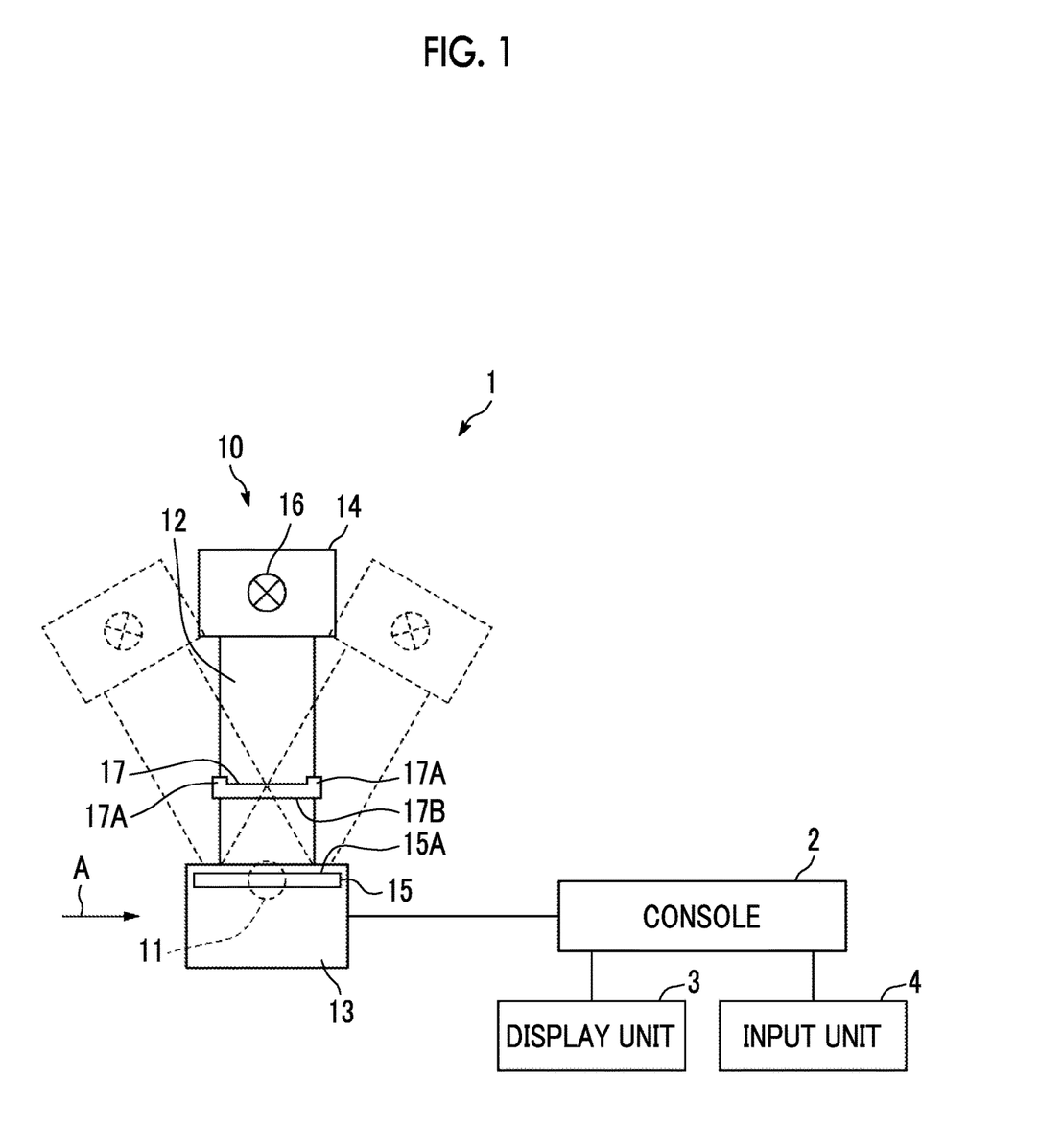
FIG. 1 is a schematic configuration diagram of a radiation image capturing system to which an image processing apparatus according to a first embodiment of the present disclosure is applied.
Figure 2:
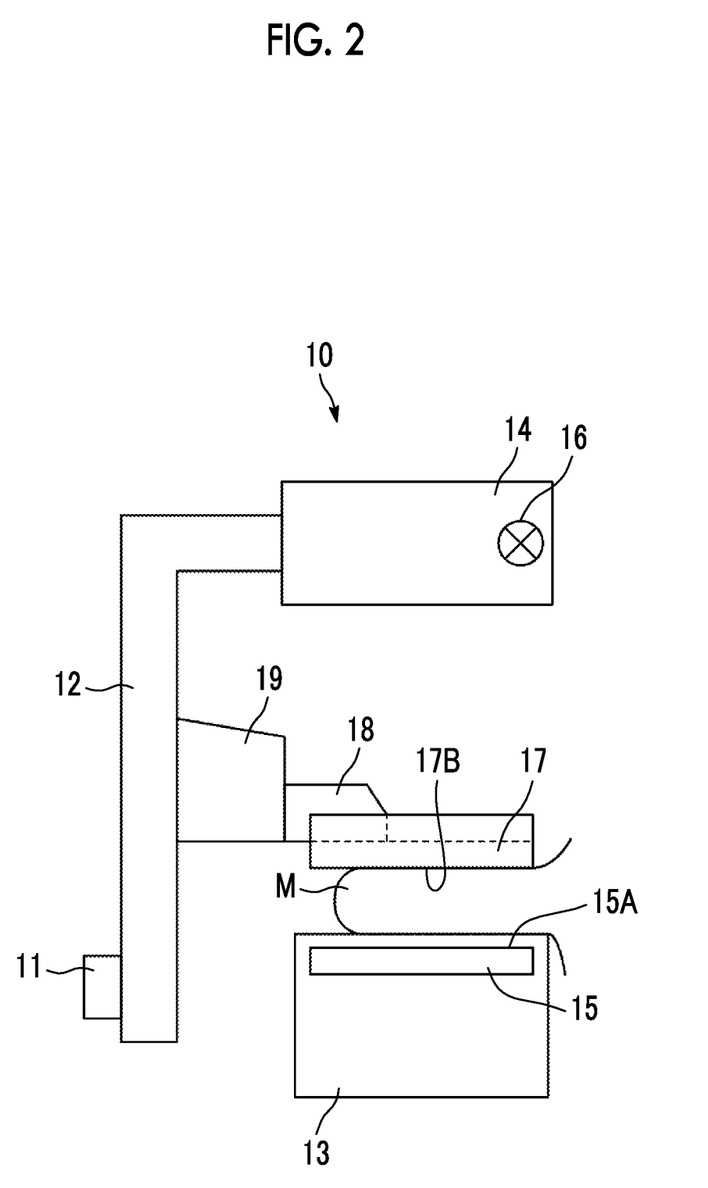
FIG. 2 is a diagram of a mammography apparatus as viewed from the direction of arrow A in FIG. 1.

Hereinafter, the embodiment of the present disclosure will be described with reference to the diagrams. FIG. 1 is a schematic configuration diagram of a radiation image capturing system to which an image processing apparatus according to a first embodiment of the present disclosure is applied, and FIG. 2 is a diagram of a mammography apparatus included in the radiation image capturing system as viewed from the direction of arrow A in FIG. 1.

As shown in FIG. 1, a radiation image capturing system 1 according to the present embodiment comprises a console 2 and a mammography apparatus 10. The console 2 comprises a display unit 3 and an input unit 4.

The radiation image capturing system 1 according to the present embodiment has a function of acquiring a breast image that is a radiation image of a breast by the mammography apparatus 10 that images the breast by an operator such as doctors and radiologists based on instructions (imaging orders) input from an external system (for example, a radiology information system (RIS)) via the console 2. In the present embodiment, the mammography apparatus 10 performs both tomosynthesis imaging and simple imaging in various imaging direction, and can generate a tomographic image of the breast and a two-dimensional breast image. The two-dimensional breast image refers to the breast image acquired by simple imaging.

The mammography apparatus 10 comprises an arm unit 12 connected to a base (not shown) by a rotary shaft 11. An imaging table 13 is attached to one end portion of the arm unit 12, and a radiation emission unit 14 is attached to the other end portion so as to face the imaging table 13. The arm unit 12 is configured so that only the end portion to which the radiation emission unit 14 is attached can rotate. Therefore, it is possible to rotate only the radiation emission unit 14 with the imaging table 13 fixed. The rotation of the arm unit 12 is controlled by the console 2.

The imaging table 13 comprises a radiation detector 15 such as a flat panel detector therein. The radiation detector 15 has a detection surface 15A of radiation. In addition, a circuit board on which a charge amplifier for converting a charge signal read from the radiation detector 15 into a voltage signal, a correlated double sampling circuit for sampling the voltage signal output from the charge amplifier, an analog digital (AD) conversion unit for converting the voltage signal into a digital signal, and the like are provided is provided inside the imaging table 13.

The radiation detector 15 can perform recording and reading of a radiation image repeatedly. A so-called direct-type radiation detector that directly converts radiation into electric charges may be used, or a so-called indirect-type radiation detector that converts radiation into visible light and then converts the visible light into a charge signal may be used. As a method of reading a radiation image signal, it is desirable to use a so-called thin film transistor (TFT) reading method in which a radiation image signal is read by ON and OFF of a TFT switch, or a so-called optical reading method in which a radiation image signal is read by emission of reading light. However, other methods may also be used without being limited to the above methods.

A radiation source 16 is housed inside the radiation emission unit 14. The radiation source 16 emits radiation such as X-rays, and the timing of emission of radiation from the radiation source 16, and a radiation generation condition in the radiation source 16, that is, selection of target and filter materials, a tube voltage, an emission time, and the like are controlled by the console 2.

The arm unit 12 includes compression plate 17 that compresses a breast M, a support unit 18 that supports the compression plate 17, and a moving mechanism 19 that moves the support unit 18 in the vertical direction in FIGS. 1 and 2. Information of the distance between the compression plate 17 and the imaging table 13, that is, a compression thickness is input to the console 2. The compression plate 17 is prepared in a plurality of sizes and shapes according to the type of imaging. The compression plate 17 is exchangeably attached to the support unit 18. Side walls 17A are formed at edges of the compression plate 17 which are positioned in right and left portions in FIG. 1. The side walls 17A are formed to reduce the pain of the patient in a case where the breast M compressed by a compression surface 17B of the compression plate 17 protrudes from the compression plate 17.

The display unit 3 is a display such as a cathode ray tube (CRT) or a liquid crystal display, and displays a message required for the operation, and the like in addition to the tomographic image and the composite two-dimensional image described later. The display unit 3 may include a speaker for outputting sound.

The input unit 4 includes an input device such as a keyboard, a mouse, or a touch panel, and receives an operation instruction of the mammography apparatus 10 by the operator. In addition, the input unit 4 receives an input of various kinds of information such as imaging conditions and correcting instruction for information, which are required to perform the tomosynthesis imaging. In the present embodiment, each unit of the mammography apparatus 10 operates according to the information input by the operator through the input unit 4.

An image processing program according to the present embodiment is installed in the console 2. In the present embodiment, the console 2 may be a workstation or a personal computer that is directly operated by the operator, or may be a server computer connected to these through a network. The image processing program is stored in a storage device of a server computer connected to the network, or in a network storage so as to be accessible from the outside, and is downloaded and installed in the computer as necessary. Alternatively, the image processing program is distributed in a state of being recorded on a recording medium such as a digital versatile disc (DVD) or a compact disc read only memory (CD-ROM), and is installed in the computer from the recording medium.

Figure 3:
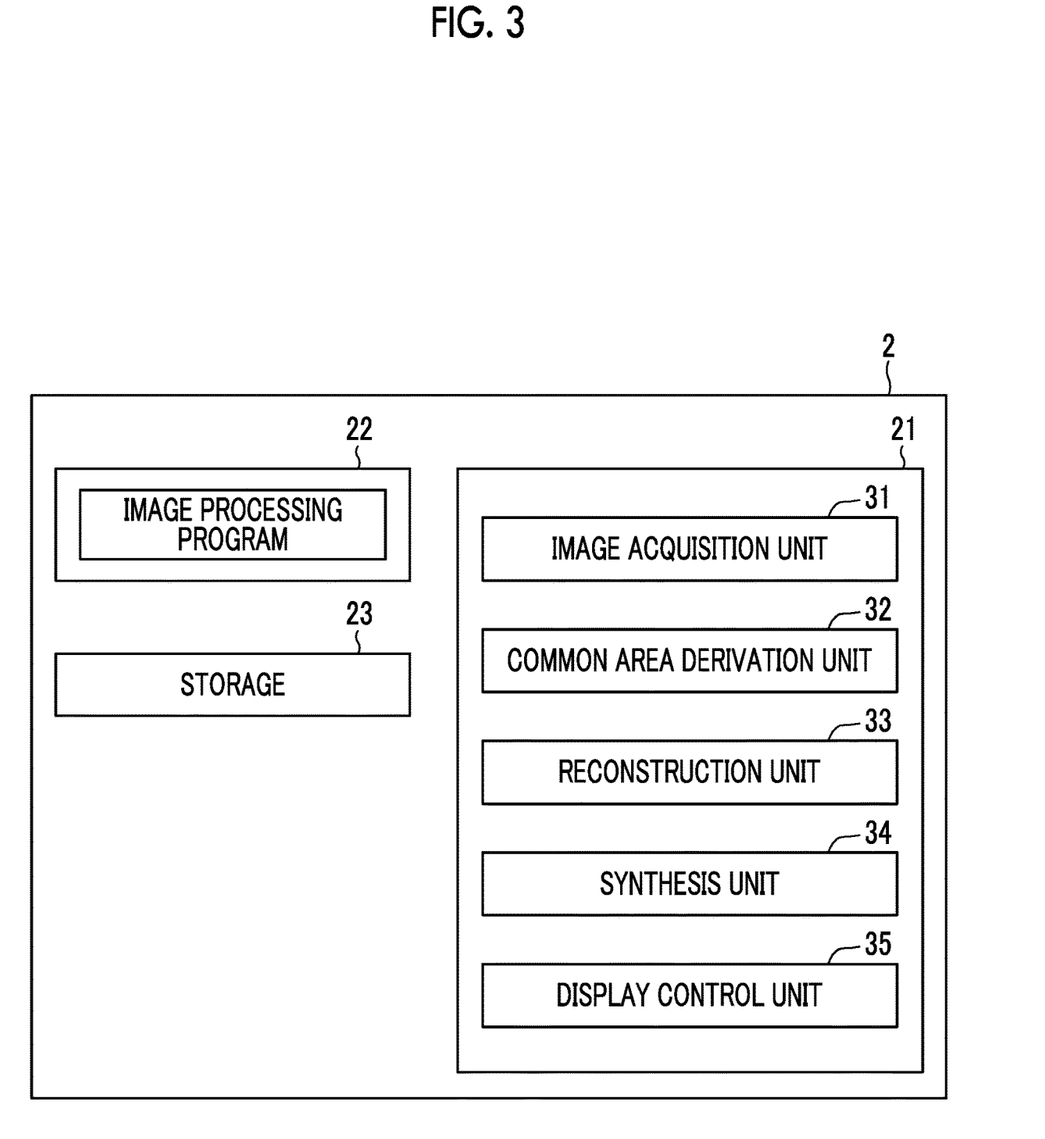
FIG. 3 is a diagram showing a schematic configuration of the image processing apparatus realized by installing an image processing program in a computer that configures a console in the first embodiment.

FIG. 3 is a diagram showing a schematic configuration of the image processing apparatus realized by installing the image processing program according to the present embodiment in a computer that configures the console 2. As shown in FIG. 3, the image processing apparatus comprises a central processing unit (CPU) 21, a memory 22, and a storage 23 as the configuration of a standard computer.

The storage 23 includes a storage device such as a hard disk drive or a solid state drive (SSD), and stores various kinds of information including a program for driving each unit of the mammography apparatus 10 and the image processing program. In addition, the storage 23 also stores the projection image acquired by imaging, and the tomographic image and the composite two-dimensional image generated as described later.

The memory 22 temporarily stores programs and the like stored in the storage 23 so that the CPU 21 executes various kinds of processing. The image processing program causes the CPU 21 to execute follows: image acquisition processing of acquiring a plurality of projection images of the breast M corresponding to a plurality of radiation source positions by tomosynthesis imaging by the mammography apparatus 10; common area derivation processing of deriving a common area common to at least a part of the plurality projection images; reconstruction processing of reconstructing the plurality of projection images to generate a plurality of tomographic images on each of a plurality of tomographic planes of the breast M as a subject; synthesis processing of generating the composite two-dimensional image from the plurality of tomographic images; and display control processing of emphasizing areas corresponding to the common area of at least a part of the plurality of tomographic images or the composite two-dimensional image and displaying at least the part of the tomographic images or the composite two-dimensional image on the display unit 3.

Then, the CPU 21 executes these kinds of processing according to the image processing program, so that the CPU 21 of the console 2 functions as an image acquisition unit 31, a common area derivation unit 32, a reconstruction unit 33, a synthesis unit 34, and a display control unit 35.

Figure 4:
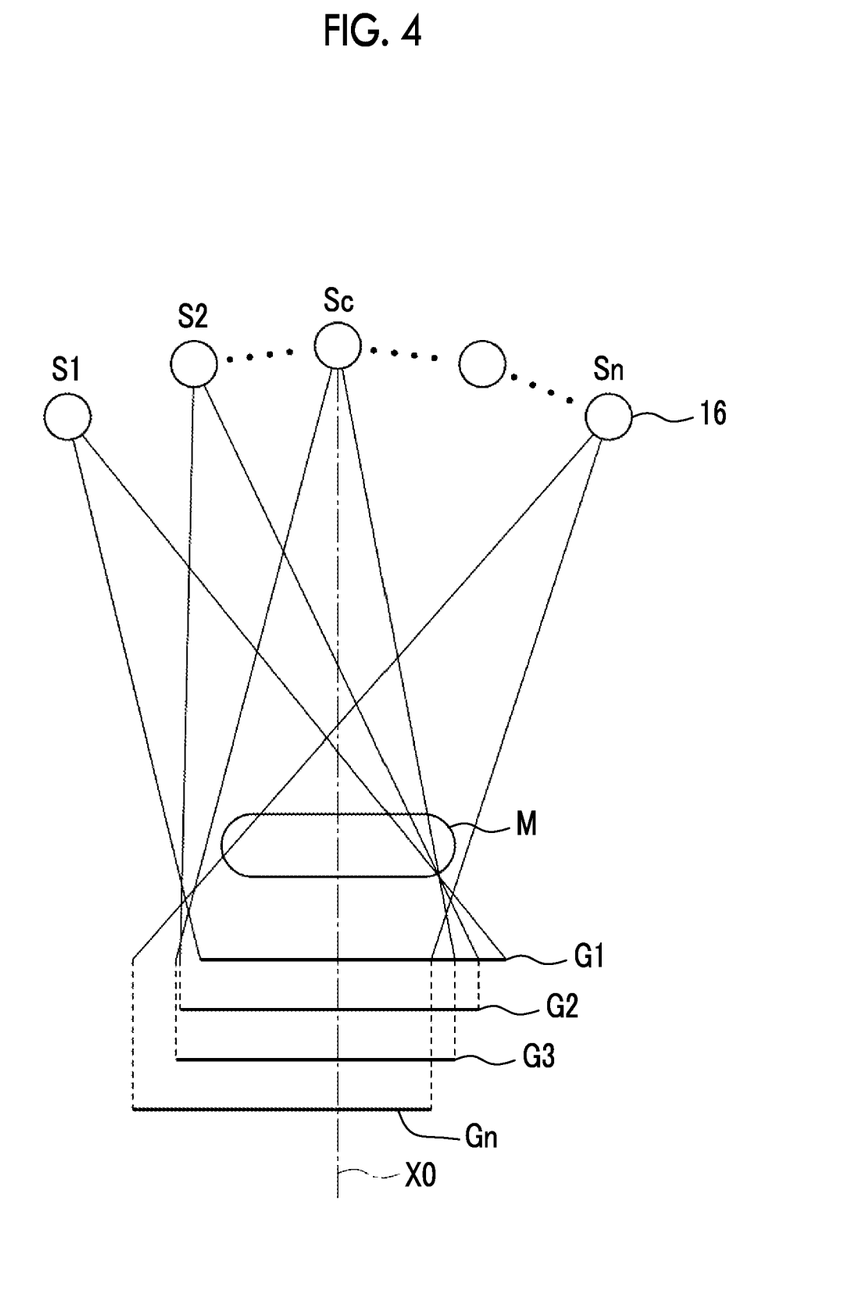
FIG. 4 is a diagram illustrating acquisition of a projection image.

The radiation source 16 is moved by rotating the arm unit 12 around the rotary shaft 11, the breast M is irradiated with radiation at a plurality of radiation source positions according to the movement of the radiation source 16 under the predetermined imaging conditions for tomosynthesis imaging, radiation transmitted through the breast M are detected by the radiation detector 15, and a plurality of projection images Gi (i=1 to n, where n is the number of radiation source positions; for example, n=15) at a plurality of radiation source positions are acquired by the image acquisition unit 31. FIG. 4 is a diagram illustrating acquisition of the projection image Gi. As shown in FIG. 4, the radiation source 16 is moved to each radiation source position of S1, S2, Sn, the radiation source 16 is driven at each radiation source position to irradiate the breast M with radiation, and the radiation transmitted through the breast M are detected by the radiation detector 15. As a result, the projection images G1, G2, . . . Gc, Gn are acquired corresponding to the radiation source positions S1 to Sn. The radiation source position Sc shown in FIG. 4 is a radiation source position where an optical axis X0 of the radiation emitted from the radiation source 16 is perpendicular to the detection surface 15A of the radiation detector 15. Hereinafter, the radiation source position Sc will be referred to as a reference radiation source position Sc. At each of the radiation source positions S1 to Sn, the breast M is irradiated with radiation of the same dose. A plurality of acquired projection images Gi are stored in the storage 23.

Figure 5:
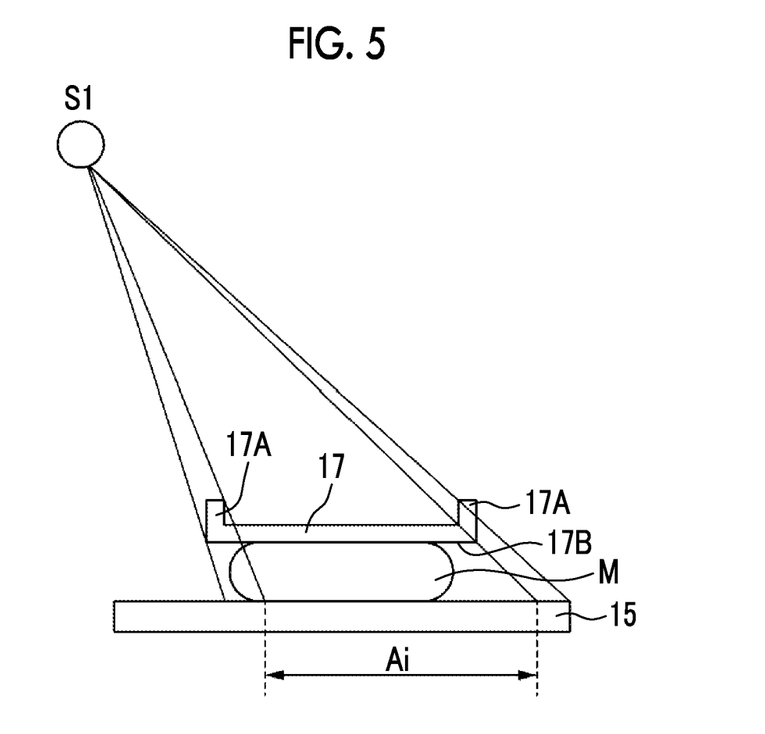
FIG. 5 is a diagram showing a geometric relationship between a radiation source, a compression plate, a breast, and a radiation detector.
Figure 6:
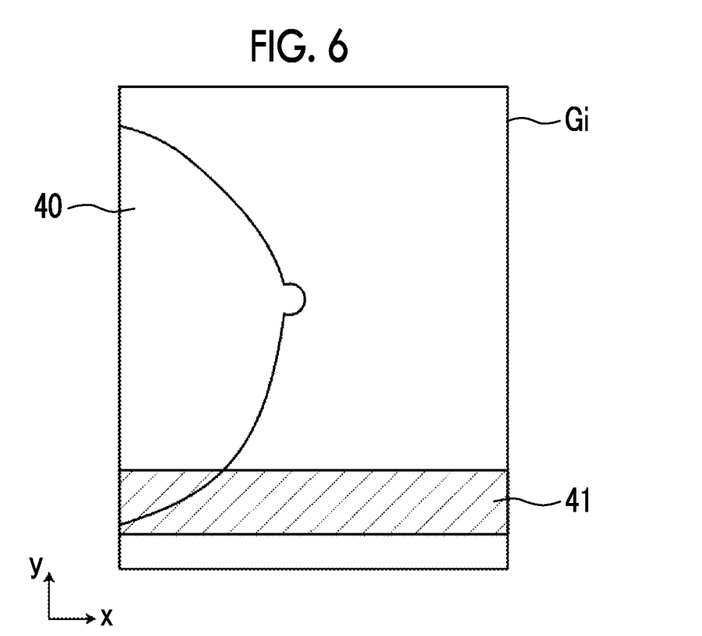
FIG. 6 is a diagram showing the projection image including an edge image.

The common area derivation unit 32 derives the common area common to at least a part of a plurality of projection images Gi. In the present embodiment, the side walls 17A are formed at edges of the compression plate 17. For this reason, in a case where the position of the radiation source 16 is inclined with respect to the vertical line to the detection surface 15A of the radiation detector 15, as shown in FIG. 5, the radiation transmitted through the side walls 17A transmits through the breast M and is detected by the radiation detector 15. In this case, in the acquired projection image Gi, as shown in FIG. 6, the band-shaped image (hereinafter, referred to as an edge image 41) caused by the side walls 17A of the compression plate 17 appears in the image of the breast M (hereinafter, referred to as a breast image 40) included in the projection image Gi. In the projection image Gi shown in FIG. 6, a coordinate system in which the movement direction of the radiation source 16 is a y direction is shown. As described above, in a case where the band-shaped edge image 41 corresponding to the side walls 17A is included in the projection image Gi, artifacts are included in the tomographic image generated by reconstructing a plurality of projection images Gi described later.

Figure 7:
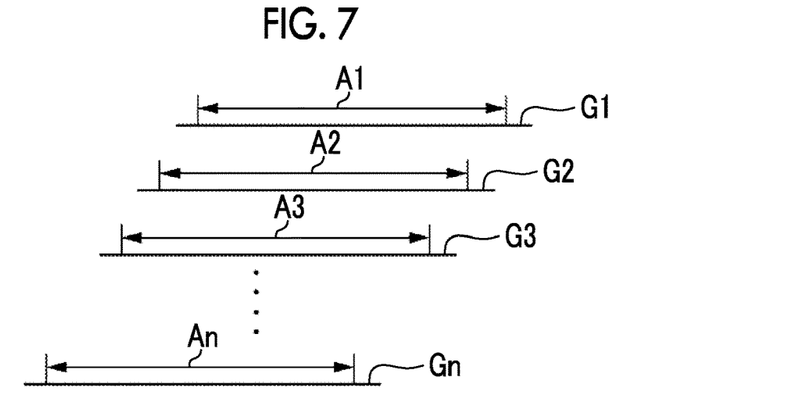
FIG. 7 is a diagram showing a required area in a plurality of the projection images.

Therefore, the common area derivation unit 32 extracts an area corresponding to the radiation transmitted through only the compression surface 17B of the compression plate 17 in a plurality of projection images Gi as a required area Ai. The required area Ai corresponds to an area where the radiation transmitted through only the compression surface 17B of the compression plate 17 in the radiation detector 15 is emitted, as shown in FIG. 5. FIG. 7 is a diagram showing the required area Ai in a plurality of the projection images Gi. As shown in FIG. 7, the required area Ai has a width excluding both edges including the edge image in the movement direction of the radiation source 16 in the projection image Gi.

Here, the size of the compression plate 17, the height and the thickness of the side walls 17A are known. The thickness of the breast M at the time of imaging is the same as the height of the compression plate 17 and is known. The position of the radiation source 16 from which each projection image Gi is acquired and the position of the detection surface 15A of the radiation detector 15 are also known. Therefore, in the present embodiment, information on the size of the compression plate 17, the height of the side walls 17A, and the thickness of the compression plate 17 is stored in the storage 23. The common area derivation unit 32 reads information on the size of the used compression plate 17, the height of the side walls 17A, and the thickness of the compression plate 17 from the storage 23, and derives the positions of both edges of the required area Ai included in the projection image Gi using a geometrical positional relationship between the thickness of the breast M at the time of imaging, the position of the radiation source 16 from which each projection image Gi is acquired, and the position of the detection surface 15A of the radiation detector 15. The common area derivation unit 32 extracts the required area Ai from the projection image Gi based on the derived position of the both edges.

Figure 8:
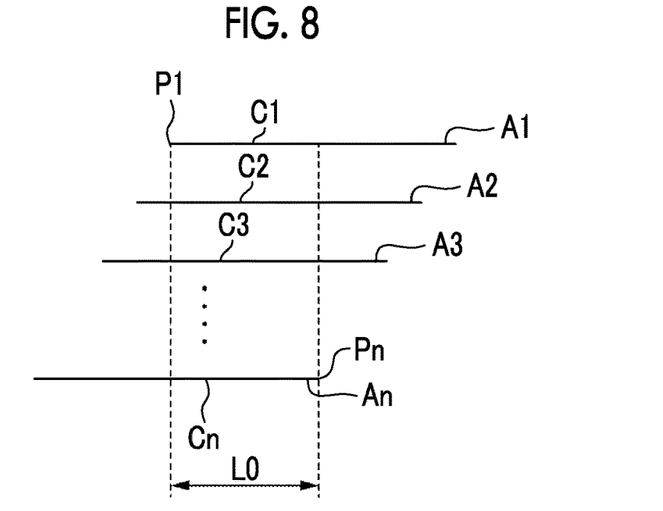
FIG. 8 is a diagram for explaining derivation of a common area Ci.

The common area derivation unit 32 derives a common area Ci common to at least a part of a plurality of projection images Gi from the required area Ai. In the present embodiment, the common area derivation unit 32 derives the common area Ci common to all of a plurality of projection images Gi, that is, a plurality of required areas Ai. FIG. 8 is a diagram for explaining derivation of the common area Ci. In order to derive the common area Ci, the common area derivation unit 32 specifies, in the detection surface 15A of the radiation detector 15, required areas A1, An of the projection images G1, Gn acquired in the radiation source positions S1, Sn. Also, the common area derivation unit 32 specifies edges P1, Pn closest to the radiation source positions S1, Sn in the required areas A1, An. As described above, the positions of both edges of the required areas A1, An are known. Therefore, the common area derivation unit 32 extracts the area having the edges P1, Pn of the required areas A1, An as both edges thereof in a plurality of required area Ai, as the common area Ci.

Figure 9:
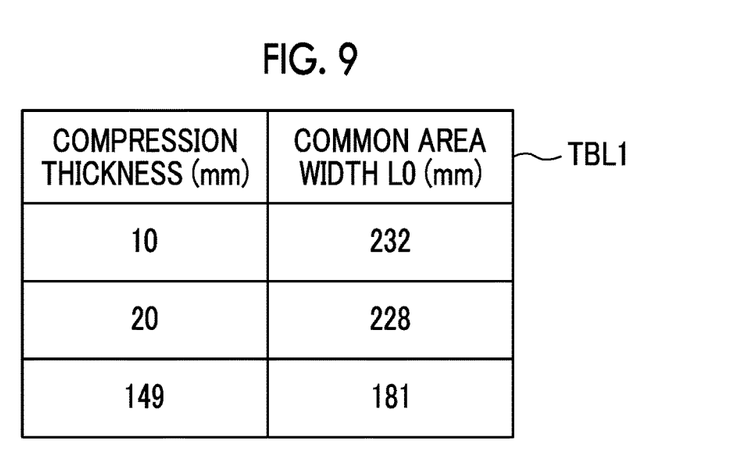
FIG. 9 is a diagram showing a table defining the relationship between a compression thickness of the breast and a width of the common area.

A width L0 of the common area Ci according to the compression thickness of the breast M in the movement direction of the radiation source 16 may be calculated in advance and stored in the storage 23 as the table. FIG. 9 is a diagram showing a table defining the relationship between the compression thickness of the breast and the width L0 of the common area Ci. In FIG. 9, the unit of the compression thickness and the width L0 is mm. A table TBL1 shown in FIG. 9 shows values in a case where, for example, the compression plate 17 is 24 cm×30 cm and the deflection angle of the radiation source 16 at the time of imaging is ±20 degrees. In a case where the compression thickness is a value other than the value shown in the table TBL1, the width L0 may be derived by an interpolation calculation using the value in the table TBL1.

Figure 10:
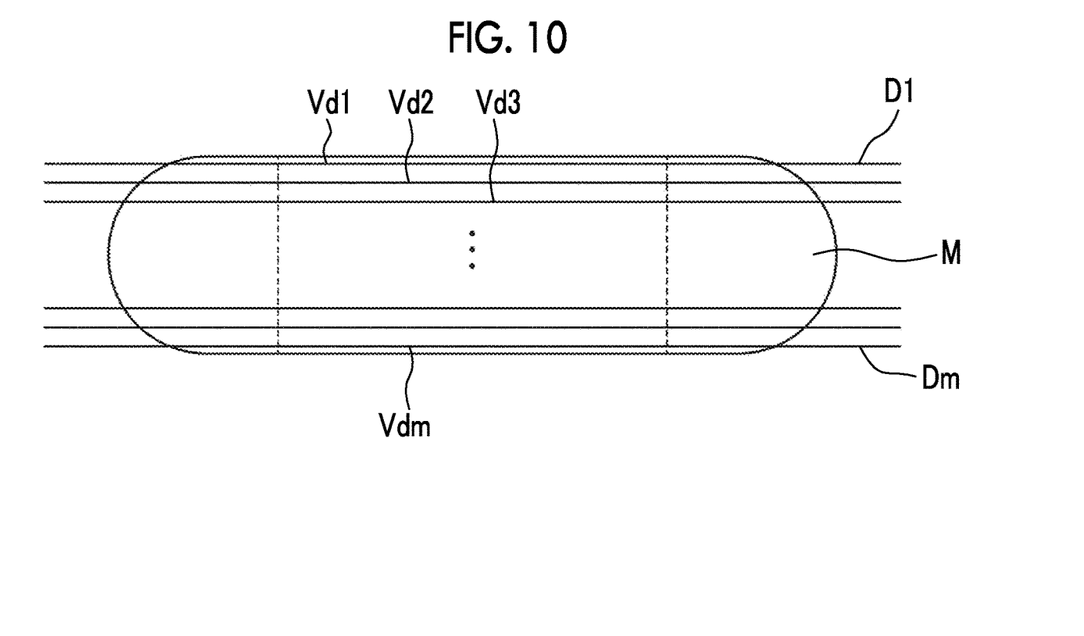
FIG. 10 is a diagram illustrating generation of a tomographic image.

The reconstruction unit 33 reconstructs the required area Ai of the projection image Gi to generate the tomographic image in which a desired tomographic plane of the breast M is emphasized. Specifically, the reconstruction unit 33 reconstructs the required area Ai of the projection images Gi by a well-known back projection method such as a simple back projection method or a filtered back projection method to generate a plurality of tomographic images Dj (j=1 to m) on each of a plurality of tomographic planes of the breast M, as shown in FIG. 10. In this case, a three-dimensional coordinate position in a three-dimensional space including the breast M is set, pixel values of corresponding pixel positions of a plurality of projection images Gi are reconstructed for the set three-dimensional coordinate position, and the pixel value of the coordinate position is calculated.

In the reconstruction, the tomographic image Dj is reconstructed for the common area Ci in the required area Ai by using all information included in the n projection images Gi.

An area corresponding to the common area Ci in the tomographic image Dj is shown in FIG. 10 as an effective image area Vdj. In the tomographic image Dj, the further away from the effective image area Vdj, the smaller the number of projection images Gi used for reconstruction, that is, the number of required areas Ai, so that the amount of information decreases, and as a result, the image quality deteriorates. Therefore, in the tomographic image Dj, the effective image area Vdj has the highest image quality in the movement direction of the radiation source 16, and the image quality gradually decreases toward the edge.

The synthesis unit 34 generates the composite two-dimensional image CG0 using a plurality of tomographic images Dj. The composite two-dimensional image CG0 is a pseudo two-dimensional image corresponding to a simple two-dimensional image captured by irradiating the breast M with radiation from the reference radiation source position Sc. In the present embodiment, the synthesis unit 34 generates the composite two-dimensional image CG0 by the addition method. The addition method is a method of weighted-adding pixel values of pixels corresponding each tomographic image Dj along the viewpoint direction from the reference radiation source position Sc to the radiation detector 15, that is, along an optical axis X0 shown in FIG. 4, in a state where a plurality of tomographic images Dj are stacked. The method of generating the composite two-dimensional image CG0 is not limited to the addition method, and a known technique can be applied. In the addition method, the weight for each pixel at the time of weighted-adding is set to 1/m in a case where m is the number of tomographic images Dj. In the composite two-dimensional image CG0, an area corresponding to the common area Ci, that is, an area corresponding to only the effective image area Vdj in a plurality of tomographic images Dj refers to an effective image area V0.

Figure 11:
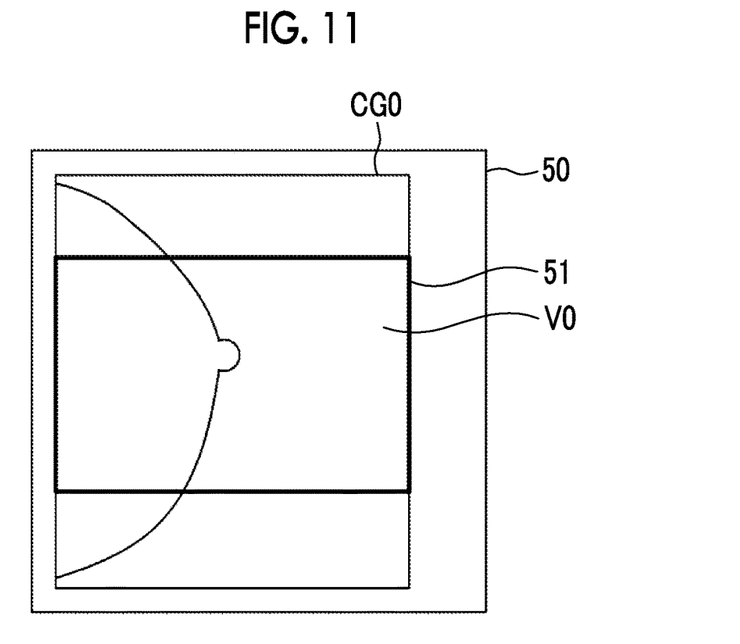
FIG. 11 is a diagram showing a display screen for a composite two-dimensional image.

The display control unit 35 displays at least a part of the tomographic image Dj or the composite two-dimensional image CG0 on the display unit 3, according to the instruction of the input unit 4. At this time, the effective image area Vdj of the tomographic image Dj and the effective image area V0 of the composite two-dimensional image CG0 are emphasized, and the tomographic image Dj or the composite two-dimensional image CG0 is displayed on the display unit 3. FIG. 11 is a diagram showing a display screen for the composite two-dimensional image CG0. As shown in FIG. 11, the composite two-dimensional image CG0 is displayed in a display screen 50. The effective image area V0 is emphasized by adding a frame 51 to the effective image area V0 of the composite two-dimensional image CG0.

Figure 12:
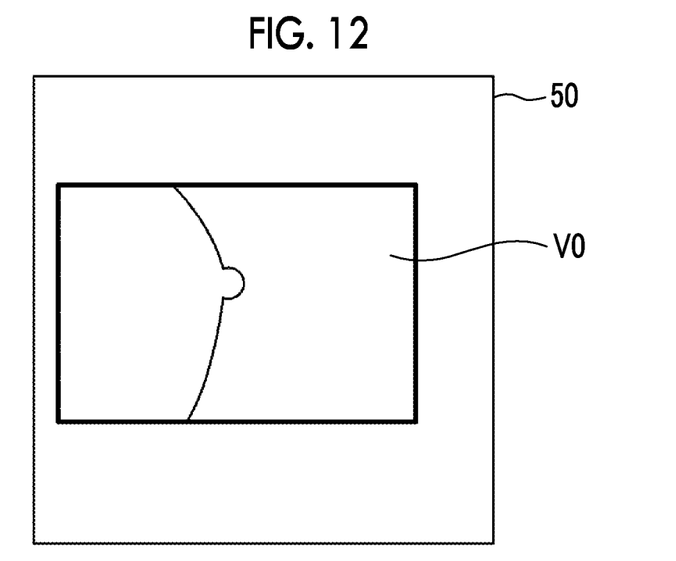
FIG. 12 is a diagram showing a display screen for the composite two-dimensional image.
Figure 13:
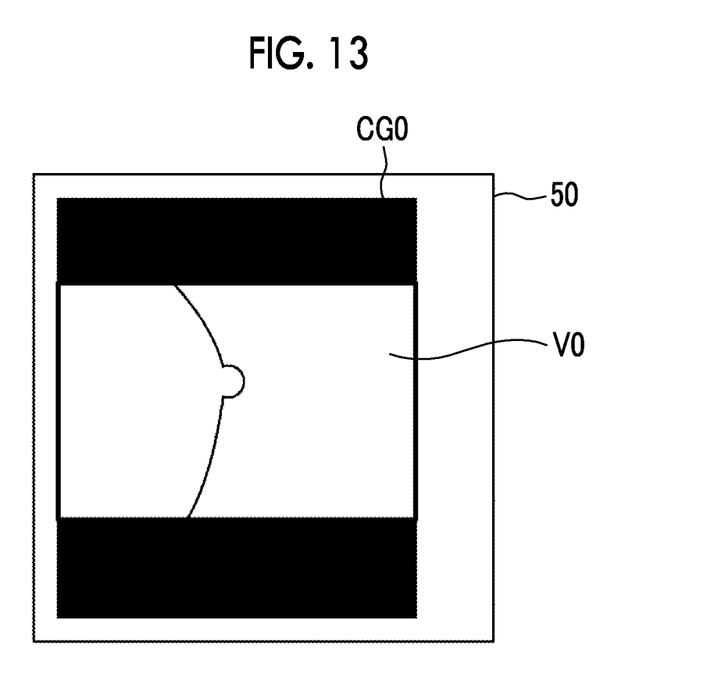
FIG. 13 is a diagram showing a display screen for the composite two-dimensional image.
Figure 14:
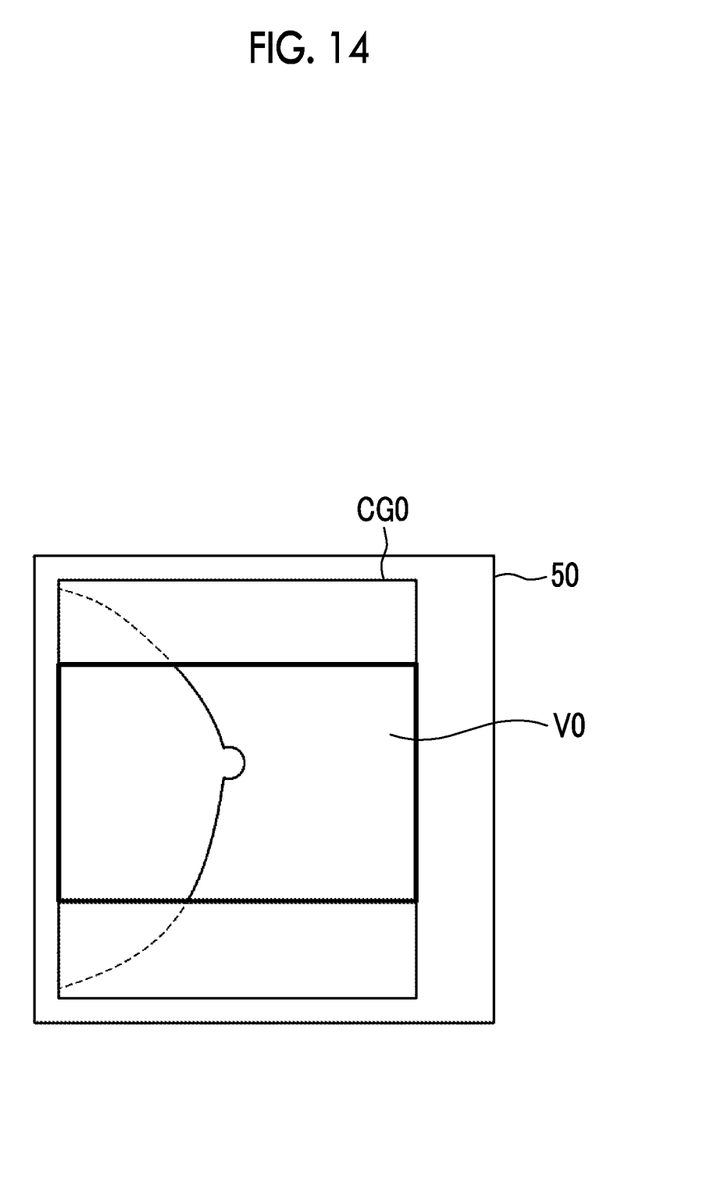
FIG. 14 is a diagram showing a display screen for the composite two-dimensional image.

As shown in FIG. 12, the display control unit 35 may emphasize the effective image area V0 by trimming only the effective image area V0 of the composite two-dimensional image CG0. As shown in FIG. 13, the display control unit 36 may emphasize the effective image area V0 by painting out an area other than the effective image area V0 of the composite two-dimensional image CG0. As shown in FIG. 14, the display control unit 36 may emphasize the effective image area V0 by reducing the concentration of an area other than the effective image area V0 of the composite two-dimensional image CG0. In FIG. 14, the outline of the breast included in the composite two-dimensional image CG0 is indicated by a broken line and the concentration is reduced.

On the other hand, in a case where the tomographic image Dj is displayed, the effective image area Vdj of each tomographic image Dj may be emphasized and displayed, as in a case where the composite two-dimensional image CG0 is displayed. The tomographic images Dj to be displayed may be all of the tomographic images or only some tomographic images.

Figure 15:
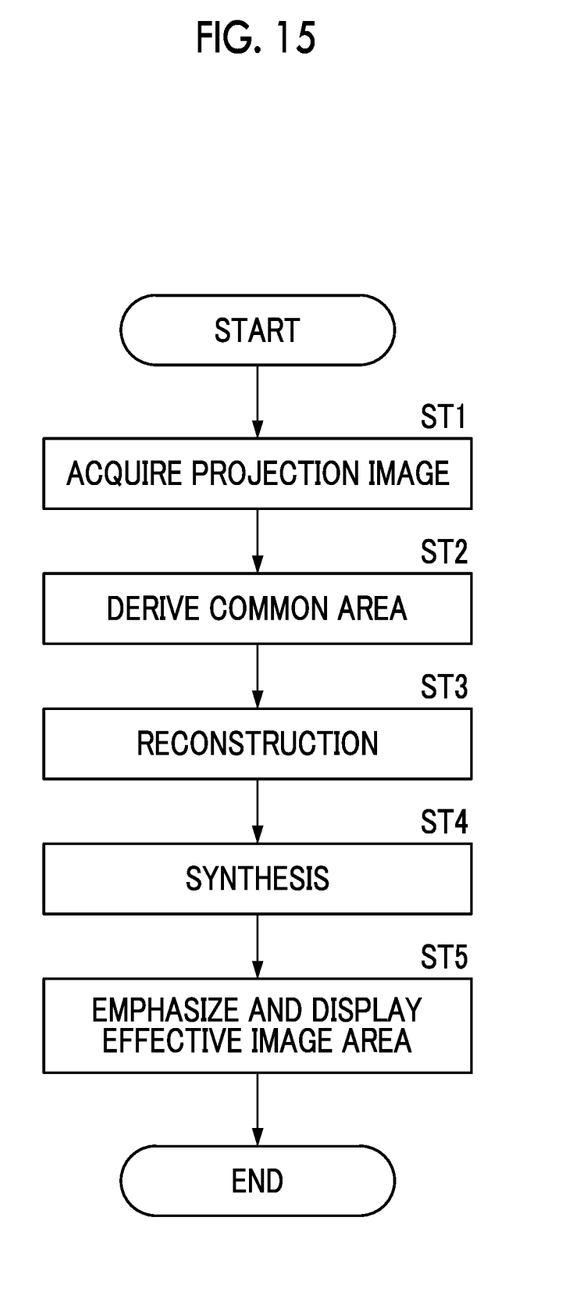
FIG. 15 is a flowchart showing processing performed in the first embodiment.

Next, the processing performed in the present embodiment will be described. FIG. 15 is a flowchart showing processing performed in the first embodiment. In a case where the instruction of an operator to start the processing is received through the input unit 4, the tomosynthesis imaging is performed and the image acquisition unit 31 acquires a plurality of projection images Gi (step ST1). The common area derivation unit 32 derives the common area common to at least a part of a plurality of projection images Gi (step ST2).

The reconstruction unit 33 reconstructs a plurality of projection images Gi to generate a plurality of tomographic images Dj in a plurality of tomographic planes of the breast M (step ST3). The synthesis unit 34 generates the composite two-dimensional image CG0 from a plurality of tomographic images Dj (step ST4). The display control unit 35 emphasizes effective image areas Vdj and V0 of at least a part of the plurality of tomographic images Dj or the composite two-dimensional image CG0 and displays at least the part of the tomographic images or the composite two-dimensional image on the display unit 3 (effective image area emphasized displaying; step ST5), processing ends.

In the present embodiment, the common area Ci common to at least a part of a plurality of projection images Gi is derived. In a case where at least a part of a plurality of tomographic images Dj which are generated by reconstructing a plurality of projection images, or the composite two-dimensional image CG0 generated from a plurality of the tomographic images is displayed on the display unit 3, effective image areas Vdj, V0 corresponding to the common area Ci are emphasized and displayed. The tomographic image Dj and the composite two-dimensional image CG0 have higher image quality as the number of areas common to the projection image Gi increases. Therefore, in the tomographic image Dj and the composite two-dimensional image CG0, the effective image areas Vdj and V0 corresponding to the common area Ci are emphasized and displayed, and thus the operator can more carefully perform image reading on an area other than the emphasized effective image area. According to the present embodiment, it is possible to reduce the possibility of missing a lesion in the tomographic image Dj acquired by tomosynthesis imaging and the composite two-dimensional image CG0.

Hereinafter, the second embodiment of the present disclosure will be described. The configuration of a radiation image processing apparatus according to the second embodiment is the same as the configuration of the radiation image processing apparatus according to the first embodiment, only the processing to be performed is different, and thus the detailed description of the apparatus is omitted.

In the radiation image processing apparatus according to the second embodiment, the processing is different from that of the first embodiment in that in a case where a width of the common area Ci in a movement direction of the radiation source 16 is equal to or greater than a predetermined threshold value, the display control unit 35 displays at least the part of the plurality of tomographic images Dj or the composite two-dimensional image CG0 on the display unit 3.

Figure 16:
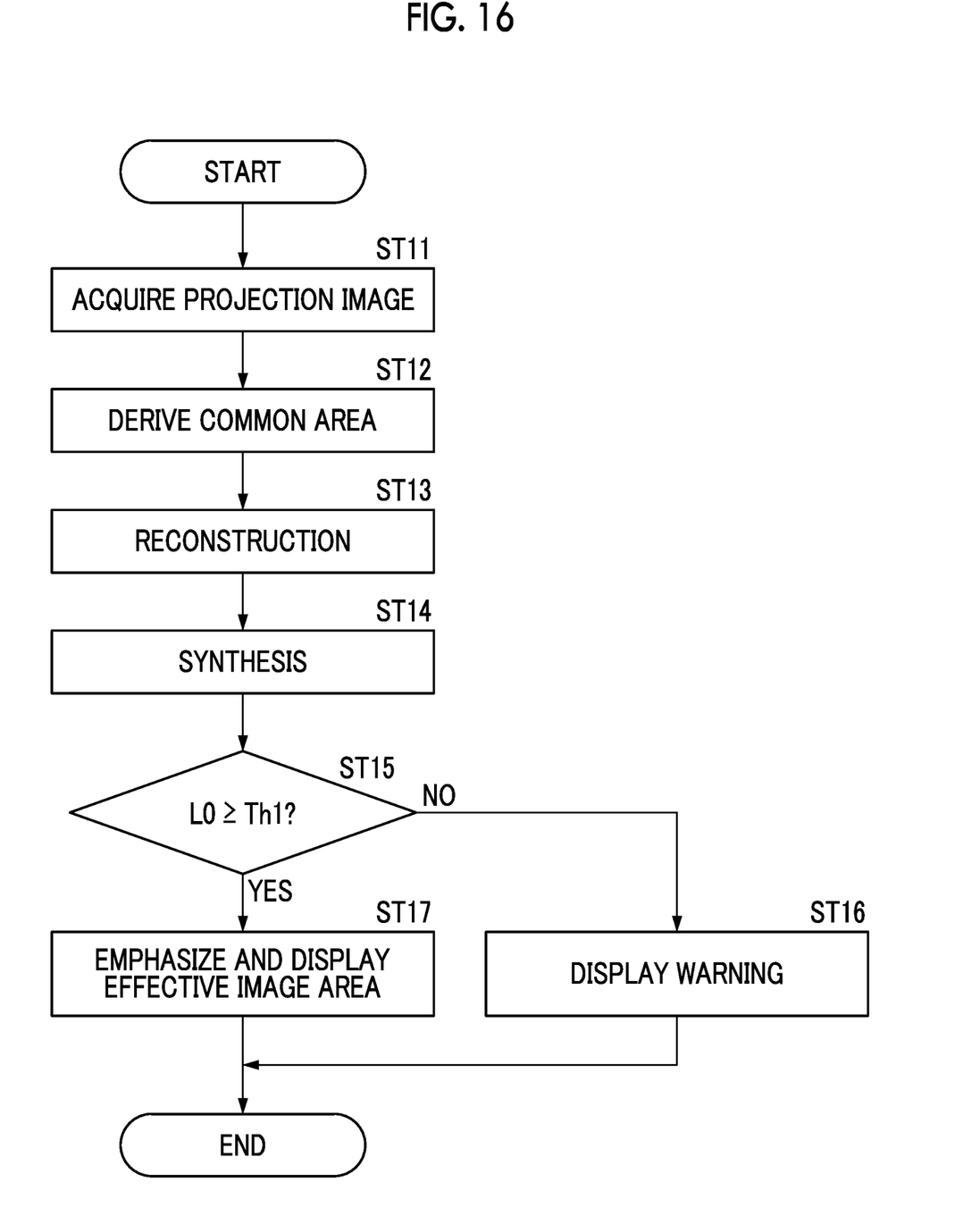
FIG. 16 is a flowchart showing processing performed in a second embodiment.

Next, the processing performed in the second embodiment will be described. FIG. 16 is a flowchart showing processing performed in the second embodiment. In a case where the instruction of an operator to start the processing is received through the input unit 4, the tomosynthesis imaging is performed, and the image acquisition unit 31 acquires a plurality of projection images Gi (step ST11). The common area derivation unit 32 derives the common area common to at least a part of a plurality of projection images Gi (step ST12).

The reconstruction unit 33 reconstructs a plurality of projection images Gi to generate a plurality of tomographic images Dj in a plurality of tomographic planes of the breast M (step ST13). The synthesis unit 34 generates the composite two-dimensional image CG0 from a plurality of tomographic images Dj (step ST14). The display control unit 35 determines whether a width of the common area in the movement direction of the radiation source 16, that is, the width L0 of the common area Ci in the state shown in FIG. 8 is equal to or greater than a predetermined threshold value Th1 (step ST15).

Figure 17:
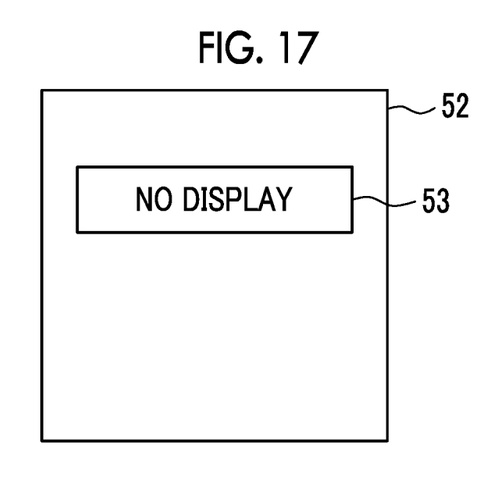
FIG. 17 is a diagram showing a displayed warning screen in the second embodiment.

In a case where the determination in step ST15 is negative, the display control unit 35 displays the warning screen on the display unit 3 (step ST16), and the processing ends. FIG. 17 is a diagram showing the displayed warning screen in the second embodiment. As shown in FIG. 17, the warning screen 52 includes a text 53 of "No display". Thereby, the operator can recognize that the tomographic image Dj or the composite two-dimensional image CG0 is not displayed.

In a case where the determination in step ST15 is positive, the display control unit 35 emphasizes effective image areas Vdj and V0 of at least a part of the plurality of tomographic images Dj or the composite two-dimensional image CG0 and displays at least the part of the tomographic images or the composite two-dimensional image on the display unit 3 (effective image area emphasized displaying; step ST17), processing ends.

In a case where the thickness of the breast M is very large, the width L0 of the common area Ci in the movement direction of the radiation source 16 becomes small In a case where the width L0 of the common area Ci is small, the proportion of the area in which the lesion is likely to be missed in the displayed image increases, and as a result, the possibility of erroneous diagnosis increases. In the second embodiment, only in a case where the width L0 of the common area Ci in the movement direction of the radiation source is equal to or greater than a predetermined threshold value Th1, at least a part of the plurality of tomographic images Dj or the composite two-dimensional image CG0 is displayed, and the width L0 is smaller than the threshold Th1, and in a case where the width L0 is smaller than the threshold value Th1, the tomographic image Dj or the composite two-dimensional image CG0 is not displayed. Therefore, the possibility of erroneous diagnosis can be reduced during image reading using the tomographic image acquired by tomosynthesis imaging and the composite two-dimensional image.

Figure 18:
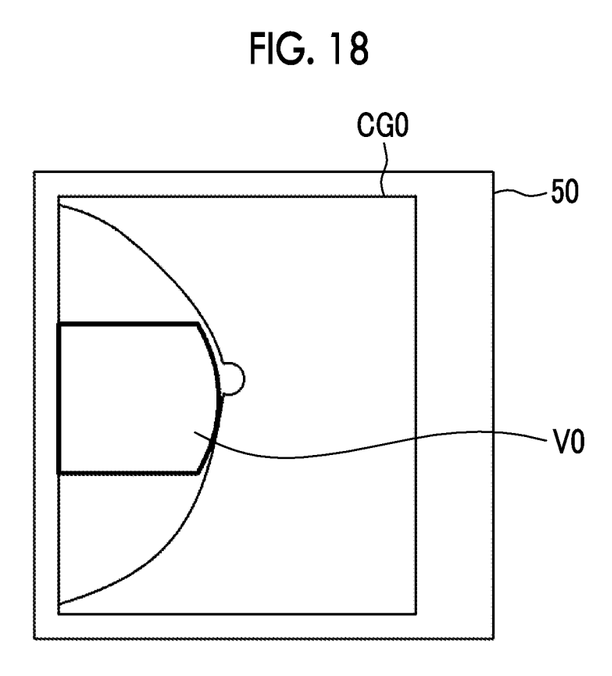
FIG. 18 is a diagram showing another example of the display screen for the composite two-dimensional image.

In the above embodiment, the radiation from the radiation source 16 is emitted so that the optical axis X0 passes near the chest wall of the breast M. For this reason, the positions of the nipples are different between the projection images G1 and Gn acquired at the radiation source positions S1 and Sn at both ends and the projection image Gc acquired at the reference radiation source position Sc. Therefore, the common area Ci may be derived in consideration of the position of the nipple of the breast M included in the projection image Gi. In this case, the effective image area V0 based on the derived common area Ci is an area where the shape on the nipple side is convex as shown in FIG. 18.

In the above embodiment, the addictive method is applied as a method of generating the composite two-dimensional image by the synthesis unit 34, but other known techniques can be applied as described above. For example, a so-called minimum path method using the minimum value of the corresponding pixels of each tomographic image may be applied.

The radiation in the above embodiment is not particularly limited, and α-rays or γ-rays can be applied in addition to X-rays.

In the above embodiment, the required area Ai is extracted from the projection image Gi, but the present invention is not limited thereto. The common area Ci may be derived without extracting the required area Ai. In this case, the generation of the tomographic image Dj is performed using the entire projection image Gi.

In the embodiment described above, for example, various processors shown below can be used as the hardware structures of processing units that execute various kinds of processing, such as the image acquisition unit 31, the common area derivation unit 32, the reconstruction unit 33, the synthesis unit 34, and the display control unit 35. The various processors include not only the above-described CPU, which is a general-purpose processor that executes software (program) and functions as various processing units, but also a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of the various processors, or may be a combination of two or more processors of the same type or different types (for example, a combination of a plurality of FPGAs or a combination of a CPU and an FPGA). Alternatively, a plurality of processing units may be configured by one processor.

As an example of configuring a plurality of processing units by one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by one or more of the above-described various processors as a hardware structure.

More specifically, as the hardware structure of these various processors, it is possible to use an electrical circuit (circuitry) in which circuit elements such as semiconductor elements are combined.

What is claimed is:

1. An image processing apparatus comprising at least one processor, wherein the processor is configured to:
   derive a common area common to at least a part of a plurality of projection images corresponding to a plurality of radiation source positions which are generated by causing an imaging apparatus to perform tomosynthesis imaging in which a radiation source is moved relative to a detection unit to irradiate a subject with radiation at the plurality of radiation source positions according to movement of the radiation source; and
   emphasize effective image areas, corresponding to the common area, of at least a part of a plurality of tomographic images representing a plurality of tomographic planes of the subject which are generated by reconstructing the plurality of projection images, or a composite two-dimensional image generated from the plurality of tomographic images, and display at least the part of the tomographic images or the composite two-dimensional image on a display;

wherein in a case where a width of the common area in a movement direction of the radiation source is equal to or greater than a predetermined threshold value, the processor is configured to display at least the part of the plurality of tomographic images or the composite two-dimensional image on the display.

2. The image processing apparatus according to claim 1, wherein in a case where the width of the common area in the movement direction of the radiation source is smaller than the predetermined threshold value, the processor is configured to display a warning screen on the display.

3. The image processing apparatus according to claim 1, wherein the processor is further configured to reconstruct the plurality of projection images to generate the plurality of tomographic images.

4. The image processing apparatus according to claim 3, wherein the processor is further configured to generate the composite two-dimensional image from the plurality of tomographic images.

5. The image processing apparatus according to claim 4, wherein the processor is configured to generate the composite two-dimensional image by weighted-adding pixel values of pixels corresponding to the plurality of tomographic images.

6. An image processing method comprising:
deriving a common area common to at least a part of a plurality of projection images corresponding to a plurality of radiation source positions which are generated by causing an imaging apparatus to perform tomosynthesis imaging in which a radiation source is moved relative to a detection unit to irradiate a subject with radiation at the plurality of radiation source positions according to movement of the radiation source; and
emphasizing effective image areas, corresponding to the common area, of at least a part of a plurality of tomographic images representing a plurality of tomographic planes of the subject which are generated by reconstructing the plurality of projection images, or a composite two-dimensional image generated from the plurality of tomographic images, and displaying at least the part of the tomographic images or the composite two-dimensional image on a display;

wherein in a case where a width of the common area in a movement direction of the radiation source is equal to or greater than a predetermined threshold value, a processor is configured to display at least the part of the plurality of tomographic images or the composite two-dimensional image on the display.

7. A non-transitory computer-readable storage medium that stores an image processing program causing a computer to execute:
a procedure of deriving a common area common to at least a part of a plurality of projection images corresponding to a plurality of radiation source positions which are generated by causing an imaging apparatus to perform tomosynthesis imaging in which a radiation source is moved relative to a detection unit to irradiate a subject with radiation at the plurality of radiation source positions according to movement of the radiation source; and
a procedure of emphasizing effective image areas, corresponding to the common area, of at least a part of a plurality of tomographic images representing a plurality of tomographic planes of the subject which are generated by reconstructing the plurality of projection images, or a composite two-dimensional image generated from the plurality of tomographic images, and displaying at least the part of the tomographic images or the composite two-dimensional image on a display;
wherein in a case where a width of the common area in a movement direction of the radiation source is equal to or greater than a predetermined threshold value, a processor is configured to display at least the part of the plurality of tomographic images or the composite two-dimensional image on the display.

* * * * *